United States Patent [19]

Friend

[11] 4,050,458
[45] Sept. 27, 1977

[54] RESPIRATION SYSTEM WITH PATIENT ASSIST CAPABILITY

[75] Inventor: Jack M. Friend, West Hollywood, Calif.

[73] Assignee: Puritan-Bennett Corporation, Kansas City, Mo.

[21] Appl. No.: 652,073

[22] Filed: Jan. 26, 1976

[51] Int. Cl.² .......................................... A61M 16/00
[52] U.S. Cl. .................................. 128/145.8; 340/240
[58] Field of Search ............... 128/145.8, 145.6, 145.5, 128/142 R, 142.2, 188, DIG. 17, DIG. 29, 2.08, 2.06 R, 2 C, 2.05 V; 340/240, 241, 239, 248 A

[56] References Cited

U.S. PATENT DOCUMENTS 3,748,656  7/1973  Gray et al. ...................... 340/239 R
3,834,382  9/1974  Lederman et al. ................. 128/145.8

Primary Examiner—Robert W. Michell
Assistant Examiner—Henry J. Recla
Attorney, Agent, or Firm—Fulwider, Patton, Rieber, Lee & Utecht

[57] ABSTRACT

A method and apparatus for initiating a positive-pressure-assisted inspiration phase in response to a patient's inspiratory effort, and independently of the absolute pressure at the time of the inspiratory effort, since the absolute pressure may vary from patient to patient or depend upon a particular mode of operation of the respiration system. The invention apparatus includes a differentiator circuit for obtaining a time-differentiated pressure signal, and a circuit for detecting a change in the sign of the slope of the differentiated signal. The patient's inspiratory effort is manifested as an increased rate of pressure drop, and this shows up as a change in the sign of the slope of the differentiated pressure, which is detected independently of absolute pressure, and is utilized to initiate an assisted inspiration phase. The apparatus also includes circuitry for detecting a predetermined drop in pressure, from the time of detection of the inspiratory effort, to ensure that minor variations in the pressure signal will not trigger a spurious inspiration phase.

8 Claims, 7 Drawing Figures

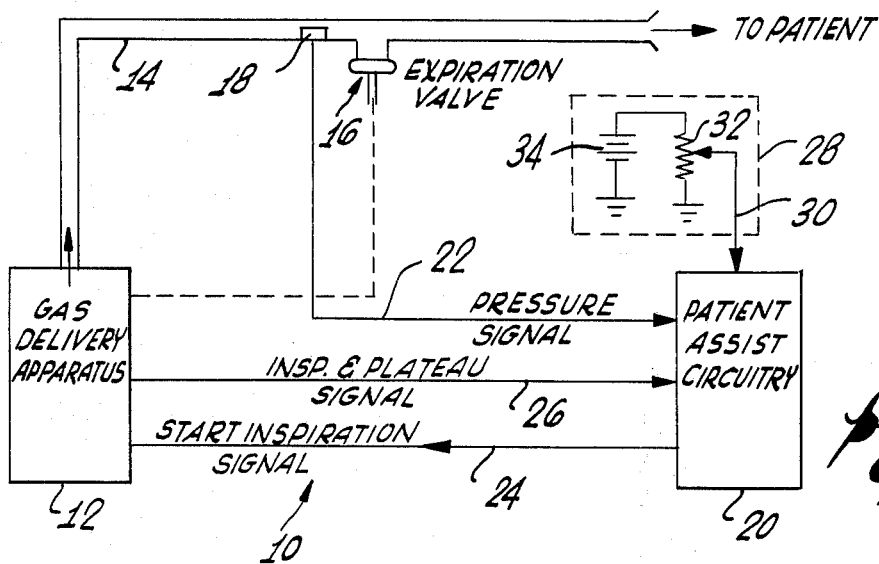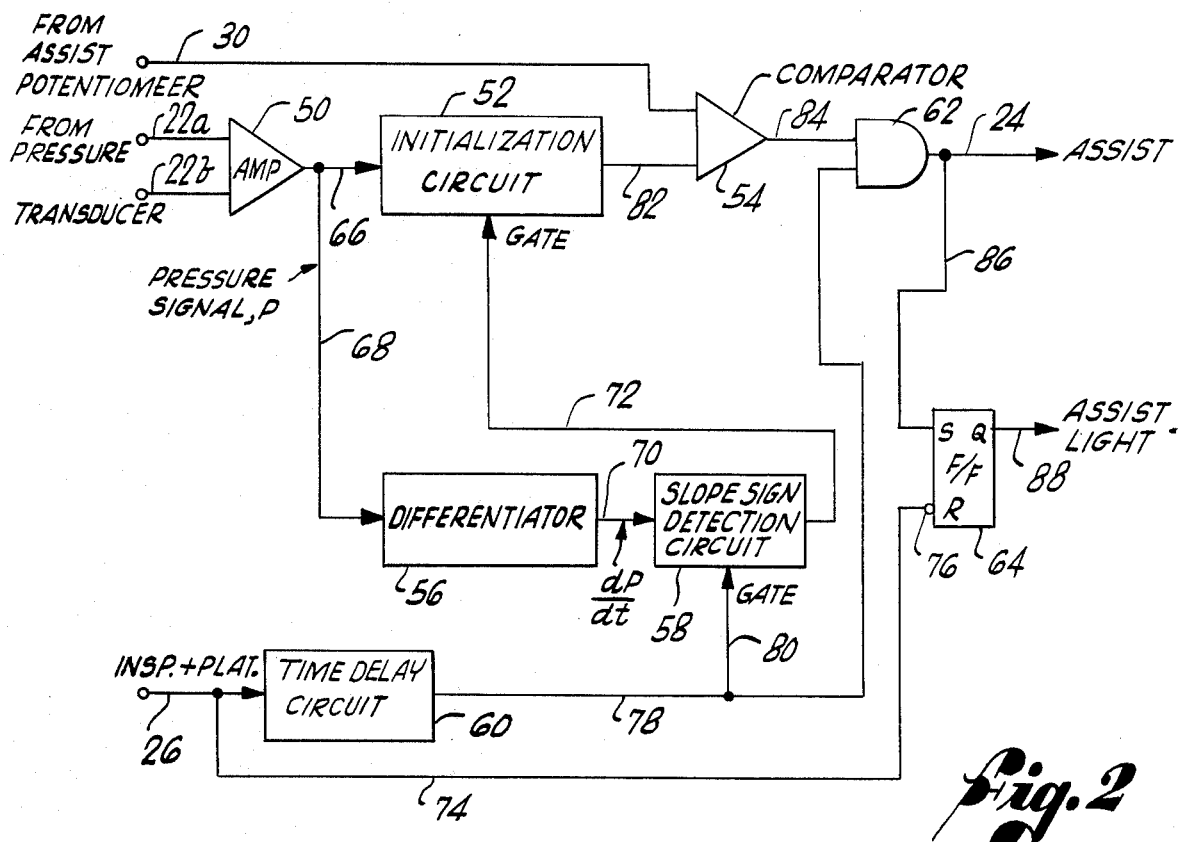

RESPIRATION SYSTEM WITH PATIENT ASSIST CAPABILITY

BACKGROUND OF THE INVENTION

This invention relates generally to respiration systems, and, more particularly, to respiration systems for the administration of intermittent positive-pressure breathing therapy, either as part of a life support system for critically ill patients, or on a regular basis for patients with certain chronic lung conditions. In a positive-pressure respirator system, the patient is supplied with air or other breathable gas mixture at a positive pressure with respect to atmospheric pressure, the positive pressure being removed to allow the patient to exhale after a desired volume has been delivered to the patient, or after a desired pressure is reached in the patient's lungs.

In situations in which the patient is incapable of initiating a breath, such systems can operate to supply the assistance of positive pressure during each inspiration phase of a timed breathing cycle. However, where the patient is capable of initiating inspiration, the application of positive pressure during inspiration is not timed, but is triggered by the patient's initial intake of a breath. Typically, in systems available heretofore, the supply of gas at positive pressure is initiated in response to the attainment of a predetermined low pressure. As is well known, the pressure at the point of delivery of the gas to the patient falls in an approximately exponential manner during the expiration phase of the breathing cycle, and when the patient takes a new breath, the pressure falls further and at an increased rate. Ideally the system should be responsive to this drop in pressure caused by the patient's intake of breath. Unfortunately, however, the absolute pressure at which this intake of breath occurs may vary from patient to patient, and even from breath to breath with the same patient. Consequently, in systems in which the positive-pressure inspiration phase is initiated in response to an absolute pressure measurement, the time of the start of the inspiration phase may not always correspond exactly with the patient's initial inspiratory effort. It will be appreciated that the patient can be caused considerable discomfort, and may lose much of the benefit of the therapy, by the application of positive pressure to his lungs either before expiration has been completed, or after he has tried to begin inhaling again.

The initiation of a positive-pressure inspiration phase based on an absolute pressure measurement is even more disadvantageous when certain variations of the basic positive-pressure system are employed. In one variation, known as "positive end expiratory pressure" (PEEP), the patient has to breathe out against a positive pressure with respect to the atmospheric pressure. This leaves the lungs at a positive pressure at the end of expiration, and inhibits lung collapse, which might occur in certain respiratory conditions. For other conditions and ailments, a variation known as "negative end expiratory pressure" (NEEP) may be employed. Here, the patient breathes out into a negative or vacuum pressure with respect to atmospheric pressure, and air is drawn from the lungs by the negative pressure. This variation might be used if the patient is unable to exhale readily because of an increased resistance to the flow of air from his lungs, or because of a weakened condition. It will be appreciated that, if the mode of operation of the respirator system is changed from the normal mode to either of the modes just described, then the absolute pressure at which the patient initiates the intake of a new breath will be different from mode to mode, and readjustment of the system will be necessary to ensure that the patient receives positive pressure at the proper time in the breathing cycle.

Accordingly, there is a need in the respiration art for a respiration system in which gas is delivered to the patient at positive pressure in response to a patient demand for a new breath, but completely independently of the absolute pressure measured at the point of delivery to the patient. The present invention fulfills this need.

SUMMARY OF THE INVENTION

The present invention resides in a novel method and apparatus for detecting the patient's initial inspiratory effort independently of the absolute pressure, and thus initiating assisted inspiration in response to patient demand.

Basically, and in general terms, the apparatus of the invention includes means for monitoring pressure in the system near the point of delivery of gas to the patient, means for differentiating a pressure signal, means for detecting a change of sign of the slope of the differentiated pressure signal, and means for generating, in response to the change of sign, a signal which initiates assisted inspiration. As mentioned earlier, the pressure during the expiration phase decays in an approximately exponential manner until the occurence of an inspiratory effort by the patient, at which time the pressure begins to drop at a more rapid rate than immediately prior to the effort. If the pressure signal is differentiated with respect to time, the initial inspiratory effort shows up as a peak in the differentiated pressure curve, since, prior to the inspiratory effort, the slope of the pressure curve decreases negatively, i.e. becomes less negative, and after the inspiratory effort, it increases negatively, i.e. becomes more negative. It can therefore be seen that the means for detecting a change in sign of the slope of the pressure differential curve will also detect the time of occurrence of the inspiratory effort. The means for detecting the change in sign of the slope of the pressure differential curve could take the form of another differentiating means, for obtaining the second differential of the pressure, or could, as in the presently preferred embodiment, take the form of a circuit for detecting the sign of the slope rather than the sign and magnitude of the slope.

Preferably, the apparatus of the invention also includes means for measuring a predetermined drop in absolute pressure after the detection of a change of sign of the slope of the pressure differential. Accordingly, the criteria for initiating assisted inspiration are a change in sign, from positive to negative, of the second differential of the pressure signal, and a predetermined drop in absolute pressure thereafter. The second criterion ensures that any aberrations of the equipment due to electrical noise and the like will be eliminated from consideration.

Ideally, the apparatus of the invention also includes means for adjusting its sensitivity, by varying the predetermined pressure drop which must take place before initiation of assisted inspiration.

In terms of a novel method, the present invention includes the steps of monitoring a pressure signal during the expiration phase of the breathing cycle, differentiating the resultant pressure signal with respect to time, detecting a change in sign of the slope of the pressure differential, and thereafter generating a control signal to initiate assisted inspiration. Preferably, the method also includes the step of detecting a predetermined pressure drop following the detection of a change in sign of the slope of the pressure differential signal, and varying the sensitivity of the apparatus by varying the predetermined drop in pressure which must be detected.

It will be appreciated from the foregoing that the present invention represents a significant advance over respirator systems of the prior art, in that it initiates assisted inspiration only in response to patient demand for a new inspiration phase, and it does so entirely independently of absolute pressure. Therefore, the system can be used on different patients, and can utilize variations of the basic positive-pressure technique, with little or no adjustment of the apparatus. Other aspects and advantages of the invention will become apparent from the following more detailed description taken in conjunction with the accompanying drawings.

BRIEF DESCRIPTION OF THE DRAWINGS

FIG. 1 is a diagrammatic view of a respiration system including the system of the present invention;

FIG. 2 is a simplified schematic block diagram of the apparatus of the present invention;

DESCRIPTION OF THE PREFERRED EMBODIMENTS

Figure 3A:
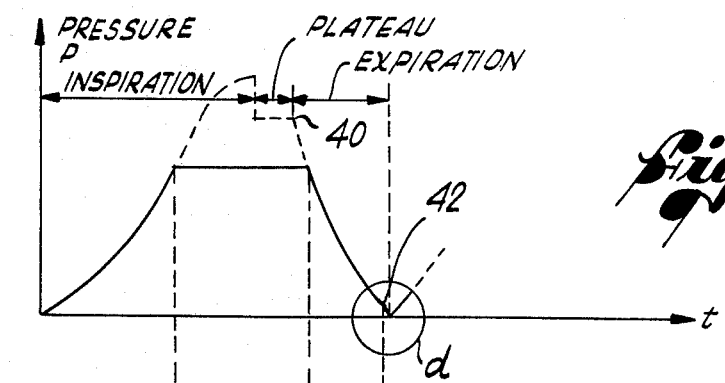
FIG. 3a is a pressure-versus-time graph taken over a typical patient breathing cycle.

As shown in the drawings for purposes of illustration, the invention is embodied in a respiration system, indicated by the reference numeral 10, for the administration of intermittent positive breathing therapy, as shown in simplified form in FIG. 1. The respiration system 10 includes gas delivery apparatus 12 for delivering air or some other breathable gas mixture to a patient undergoing the therapy, through a tube 14 from the gas delivery apparatus to the patient. The gas is normally delivered through a face mask, tracheal tube, or other means, none of which are shown. In positive-pressure breathing systems, the breathing gas is delivered to the patient at a positive pressure with respect to atmospheric pressure, until a predetermined volume has been delivered, or until the pressure in the patient's lungs reaches a predetermined value. The positive pressure from the gas delivery apparatus 12 is then removed, and an expiration valve 16, also connected to the tube 14 to the patient, is subsequently opened, allowing the patient to exhale.

In some situations, inspiration assisted by a positive pressure is initiated on a timed and cyclic basis, as is the case when the patient is unable to initiate a breath. However, so long as the patient is able to initiate an inspiratory effort by a slight intake of breath at the end of an expiration phase, the assisted inspiration phase is not usually initiated on a timed basis, but rather is responsive in some way to the patient's inspiratory effort. Typically, respiration systems of this general type utilize a pressure transducer, indicated at 18 in the delivery tube 14 to the patient, and depend upon the detection of a preselected low pressure for determining when to begin the assisted inspiration phase. Such pressure-driven systems have the significant disadvantage that the absolute pressure at which the patient initiates an inspiratory effort may vary over a time for the same patient, and will certainly vary from patient to patient, and when the system is switched to a different mode of operation, for example, requiring the patient to exhale against a pressure which is different from atmospheric.

In accordance with the present invention, the assisted inspiration phase is initiated independently of the absolute pressure, but in direct response to the patient's inspiratory effort. This is accomplished by differentiating the pressure signal derived from the pressure transducer 18 with respect to time, and detecting a change in slope, from positive to negative, in the differentiated pressure waveform, this change in slope corresponding with the beginning of the inspiratory effort of the patient. In very general terms, the apparatus of the invention, as shown in FIG. 1, includes patient assist circuitry 20 which is provided with a pressure signal over line 22 from the pressure transducer 18, and which generates a signal indicating that the assisted inspiration should be started, on line 24 to the gas delivery apparatus 12. The patient assist circuitry 20 also receives a logical signal from the gas delivery apparatus 12 on line 26, indicating whether the apparatus is in the inspiration phase, or in a plateau phase between the inspiration and expiration phases. (See FIG. 3a) Also included is a sensitivity control 28 for the patient assist circuitry 20, connected thereto over line 30, the sensitivity control principally comprising a potentiometer 32 and a voltage source 34.

The principles of operation of the invention will be readily apparent from the graphs illustrated in FIGS. 3a–3d. The pressure curve in FIG. 3a shows how the pressure, as measured at the transducer 18 (FIG. 1), varies over a typical patient breathing cycle, including an inspiration phase, a plateau phase, and an expiration phase. During the inspiration phase, the pressure rises fairly rapidly and levels off at a maximum value at which inspiration is terminated. During the plateau phase, further inspiration is prevented, but expiration is also delayed and the pressure falls rapidly to approximately the lung pressure. Then, after the expiration valve 16 is opened, as indicated at 40, the expiration phase begins, and the pressure falls in an approximately exponential manner. When the pressure has fallen to a relatively low value, the patient may initiate an inspiratory effort by a sudden intake of breath. This will have the effect of abruptly increasing the rate at which the pressure is falling during the expiration phase, as shown at 42, and as further shown in enlarged form in FIG. 3d.

Figure 3B:
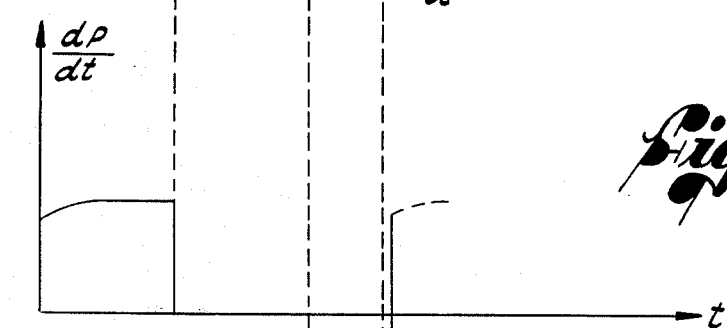
FIG. 3b is a graph drawn to the same time scale as FIG. 3a, of the pressure differentiated with respect to time.

The pressure curve illustrated in FIG. 3a has been clipped to a maximum value, consistent with the presently preferred embodiment of the invention. FIG. 3b shows the corresponding values of the differential of pressure with respect to time. It will be seen that, during the expiration phase, which is the one most important insofar as the present invention is concerned, the knee 42 of the pressure curve on FIG. 3a shows up as a peak in the pressure differential curve, as shown at 44. This, of course, is because the slope of the pressure curve prior to the inspiratory effort is continually decreasing negatively, and the slope of the pressure curve immediately after the start of the inspiratory effort increases negatively. Consequently, the knee 42 of the curve of FIG. 3a results in the relatively abrupt peak 44 of the pressure differential curve of FIG. 3b. It will be appreciated from the description thus far that the inspiratory effort can be reliably detected by monitoring the time differential of the pressure curve for an abrupt change of slope from positive to negative, and that the detection by this means will be totally independent of the absolute pressure at the time of the inspiratory effort.

As shown in FIG. 2, the patient assist circuitry 20 (FIG. 1) comprises an amplifier 50, an initialization circuit 52, the function of which will shortly be explained, a comparator 54, a differentiator 56, a slope sign detection circuit 58, a time delay circuit 60, an AND gate 62, and a flip-flop 64. The pressure signals from the transducer 18 (FIG. 1) are connected by lines 22a and 22b to the amplifier 50, the output of which is a signal proportional to the pressure measured at the pressure transducer. The pressure signal is transmitted over line 66 to the initialization circuit 52, and also over line 68 to the differentiator 56. The output of the differentiator 56 is connected by line 70 to the slope sign detection circuit 58, the output of which is connected by line 72 to gate the initialization circuit 52.

The inspiration-or-plateau signal on line 26 from the gas delivery apparatus 12 (FIG. 1) is connected to the time delay circuit 60, and is also connected by line 74 through an inverter, indicated by the circle 76, to the reset terminal of the flip-flop 64. The output of the time delay circuit 60 is connected by line 78 as one input to the AND gate 62, and by line 80 to gate the slope sign detection circuit 58. The output of the initialization circuit 52 is connected by line 82 to one input of the comparator 54, the other input being supplied over line 30 from the potentiometer 32 of the sensitivity control 28 (FIG. 1). The output of the comparator 54 is connected by line 84 to the other input of the AND gate 62, the output of which provides the assist or start-inspiration signal on line 24 to the gas delivery apparatus 12 (FIG. 1). The start-inspiration signal is also connected, by line 86, to the set terminal of the flip-flop 64. The Q output of the flip-flop 64 is used to energize an assist indicator light, as shown at 88.

Figure 3C:
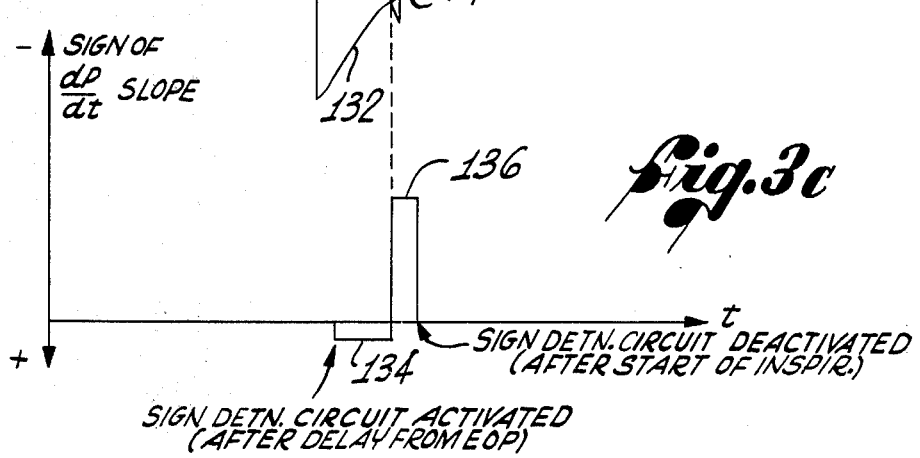
FIG. 3c is a graph drawn to the same time scale as FIGS. 3a and 3b, showing the output signal from circuitry for the detection of the sign of the slope of the pressure differential curve of FIG. 3b.
Figure 3D:
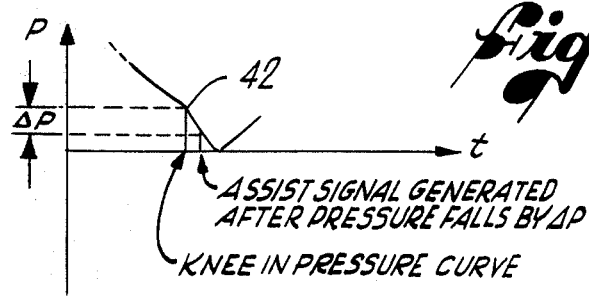
FIG. 3d is an enlarged view of that portion of the pressure curve of FIG. 3a shown in the circle "d"

The output of the differentiator 56 is basically the same as shown in FIG. 3b, and the slope sign detection circuit 58 operates to detect the change in sign, from positive to negative, in the slope of the pressure differential curve. The time delay circuit 60 is utilized to produce a gating signal on line 80 to the slope sign detection circuit 58 at an appropriate time in the expiration cycle. The state of the inspiration-or-plateau signal on line 26 changes from a logical "one" to a logical "zero" at the end of the plateau phase, and the time delay circuit 60 will generate an appropriate gating signal at a time corresponding to a point on the expiration curve shown in FIG. 3a, i.e., following the clipped portion of the pressure waveform, to enable the slope sign detection circuit 58 when the inspiratory effort is expected. After the slope sign detection circuit 58 is gated, and as will be explained in connection with the corresponding detailed circuitry, it provides an output on line 72 which is indicative of the sign of the slope of its input signal on line 70, i.e., is indicative of the sign of the slope of the pressure differential signal. In fact, as shown in FIG. 3c, the output of the slope sign detection circuit 58 on line 72 assumes a negative value immediately on gating of the circuit, and abruptly switches to a positive value when the slope of the input signal changes from positive to negative.

The initialization circuit 52 maintains a zero output on line 82 until it is gated by a positive signal on line 72. After gating, the output of the initialization circuit 52 represents the change in the input signal on line 66 since the time of gating. Stated another way, the output of the initialization circuit 52 is referenced to a zero value at the time of gating, so that its output on line 82 represents the change in absolute pressure since the time of detection of the change in sign of the slope of the differentiated pressure, i.e., since the time of the beginning of an inspiratory effort by the patient. This pressure drop on line 82 is compared with a signal representative of a predetermined pressure, as set by the potentiometer 32 of the sensitivity control 28 (FIG. 1), and an output from the comparator 54 is generated only when the pressure drop reaches the predetermined value. The output signal on line 84 from the comparator 54 is gated through the AND gate 62 provided the time delay has run out, and the start-inspiration signal is generated at the output of the AND gate on line 24. Simultaneously, the flip-flop 64 is set, thus turning on an assist indicator light, the flip-flop being reset and the indicator light extinguished at the end of the next plateau phase.

The purpose of the initialization circuit 52 and the comparator 54 is to confirm that a definite inspiratory effort has been detected by the apparatus. It is conceivable that the differentiator 56 and the slope sign detection circuit 58 could produce a positive output on line 72 as a result of electrical noise in the system, or abnormalities in the pressure transducer 18 (FIG. 1). Accordingly, the detection of a change in the sign of the second differential of the pressure has to be followed by a subsequent detection of a predetermined drop in absolute pressure before the assist signal is generated. The required drop in absolute pressure can be appropriately varied by the sensitivity control 28 (FIG. 1) to ensure that the system is insensitive to noise, and responds only to a genuine inspiratory effort by the patient.

Figure 4:
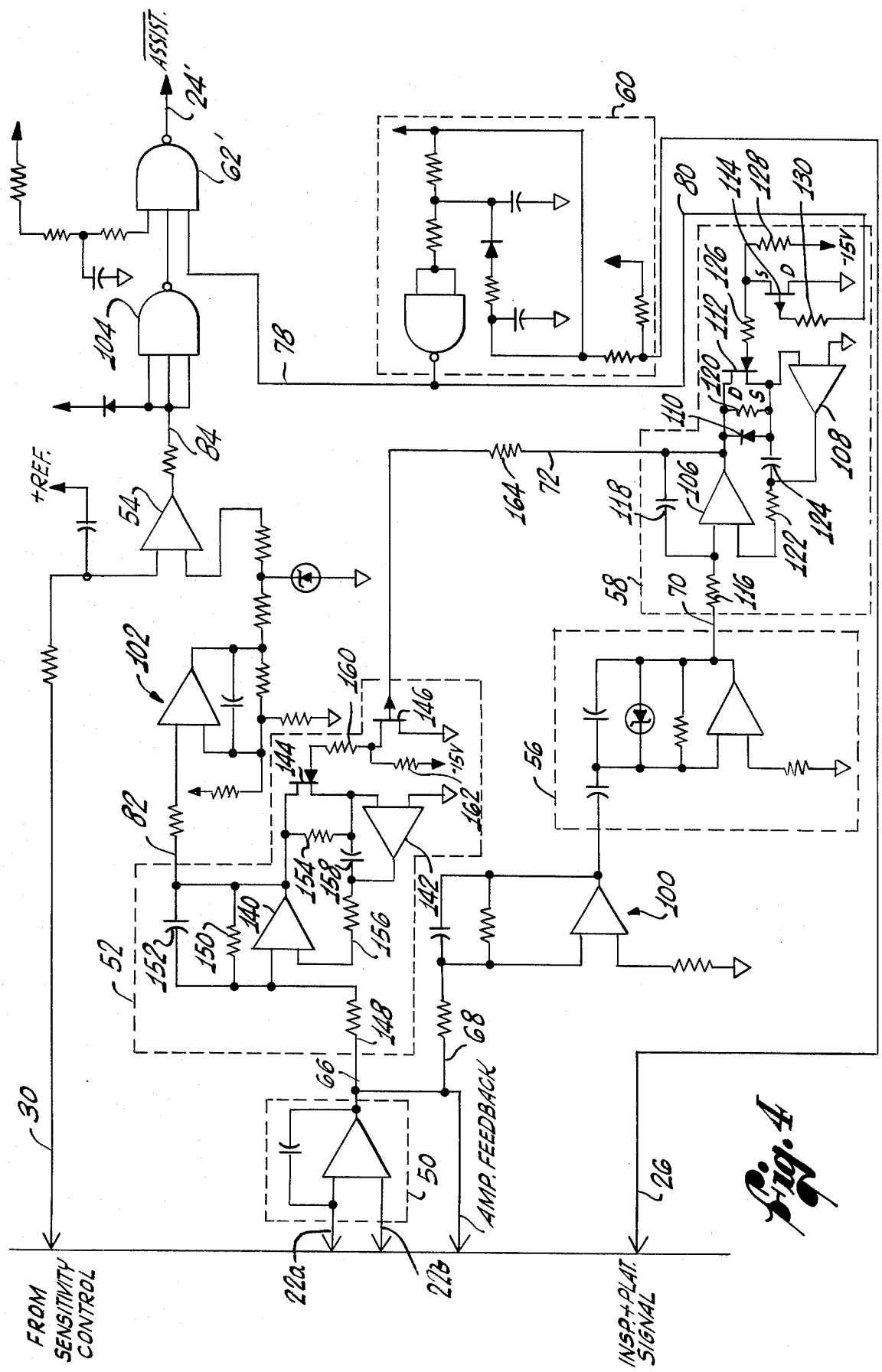
FIG. 4 is a detailed schematic view of the apparatus shown in FIG. 2.

FIG. 4 shows the apparatus of the invention in detail, and, where possible, corresponding parts in FIG. 4 and FIG. 2 are referred to by the same reference numerals. Accordingly, it will be seen that the detailed circuitry in FIG. 4 includes the amplifier 50, the diferentiator 56, the slope sign detection circuit 58, the time delay circuit 60, the initialization circuit 52, the comparator 54, and a NAND gate 62' which is equivalent in function to the AND gate 62 (FIG. 2). Also included are two further amplifiers 100 and 102, a NAND gate 104 connected as an inverter, and various other discrete components to be described. The details of the flip-flop 64 (FIG. 2) and other circuitry relating to the assist indicator light have been omitted, for clarity, from the detailed schematic, as have various other design details such as power supplies. The part numbers given in FIG. 4 are exemplary only, and are standard in the semiconductor industry.

It is believed that, for the most part, the invention can be readily practiced by one of ordinary skill in the electronics art, using only FIGS. 1–3d and the corresponding description herein. Accordingly, the corresponding detailed circuitry of the amplifiers 50, 100 and 102, comparator 54, differentiator 56, and time delay circuit 60 will not be discussed in detail, since these may be implemented in any of a variety of different designs, and the designs actually employed and illustrated are not believed to be critical to the invention. However, the initialization circuit 52 and the slope sign detection circuit 58 are of sufficient importance to the invention that the detailed designs of these should be described.

The pressure signal derived from amplifier 50 is further amplified, and inverted, in amplifier 100, and is differentiated, and again inverted, in the differentiator 56. During the amplification stages, the pressure signal is clipped to a maximum value, as shown in FIG. 3a, so that the differentiated pressure signal appears substantially as shown in FIG. 3b, and this is the signal applied over line 70 to the slope sign detection circuit 58.

The slope sign detection circuit 58 includes two operational amplifiers 106 and 108, a diode 110, an n-channel field-effect transistor (FET) 112, and a p-channel FET 114. The input signal on line 70 is connected through a resistor 116 to the negative input terminal of the first operational amplifier 106, the output terminal of which is connected through a feedback capacitor 118 to the negative input terminal, and provides the output signal of the slope sign detection circuit 58 on line 72.

The output of the first operational amplifier 106 is also connected to the negative input terminal of the second operational amplifier 108, through three parallel paths: through the diode 110, of which the cathode is connected to the output terminal of the first operational amplifier 106, through a resistor 120, and through the n-channel FET 112, of which the drain terminal is connected to the output of the first operational amplifier 106 and the source terminal is connected to the negative input terminal of the second operation amplifier 108. The positive input terminal of the second operational amplifier 108 is grounded, and the output terminal is connected through a resistor 122 to the positive input terminal of the first operational amplifier 106. The second operational amplifier 108 also has a feedback capacitor 124 between its output and negative input terminals. The gate terminal of the n-channel FET 112 is connected to a negative power supply through two series-connected resistors 126 and 128, and the source terminal of the p-channel FET 114 is connected to the junction of the two resistors. The drain terminal of the p-channel FET 114 is grounded, and the gate terminal is supplied with the delayed timing signal from the time delay circuit 60, over line 80 and through a resistor 130.

Before the timing signal is received on line 80 from the time delay circuit 60, the p-channel FET 114 is in a conductive state, so that the gate terminal of the n-channel FET 112 is essentially grounded and the n-channel FET is also in a conductive state. The second operational amplifier 108 and its feedback capacitor 124 function essentially as an integrator circuit, generating at the positive input of the first operational amplifier 106 a voltage signal which is proportional to the negative of the time integral of the first operational amplifier's 106 output. It can be seen that this has the effect of holding the output of the first operational amplifier 106 at zero, regardless of the value of the input signal on line 70. When the delayed timing signal is applied to the gate of the p-channel FET 114, this FET is rendered nonconductive, and a negative bias is applied to the gate of the n-channel FET 112, which is also rendered nonconductive as a result.

At the point in time at which the n-channel FET 112 is opened, the pressure differential signal input on line 70 will have a positive slope, as shown at 132 in FIG. 3b. Since the signal applied to the negative input terminal of the first operational amplifier 106 is, at this point in time, becoming less negative, the output of the first operational amplifier 106 will go more negative, and will become a negative as possible, limited only by the other circuit elements involved. The limiting element in this case is the diode 110, which, as has been described, has its cathode connected to the output terminal of the first operational amplifier 106 and its anode connected to the negative input terminal of the second operational 108. As the output of the first operational amplifier 106 tends to go negative, the diode is forward biased and is in a conductive state. Consequently, the voltage drop across it cannot exceed some small value, typically 0.6 volts, and the voltage at the output of the slope sign detection circuit 58 will therefore assume a small negative value, as indicated at 134 in FIG. 3c.

When the sign of the slope of the pressure differential curve changes from positive to negative, the signal input to the first operational amplifier 106 then becomes increasingly negative, so that the output on line 72 becomes increasingly positive, as shown at 136 in FIG. 3c. The diode 110 is then reverse biased and nonconductive, and the time constant of the integrator circuit is relatively large, as determined by the relatively large value of the resistor 120, so that the effect of the feedback of the integrated signal is minimal as compared with the effect of the input signal to the negative input terminal of the first operational amplifier 106. Consequently, the output of the first operational amplifier 106, and of the slope sign detection circuit 58, assumes a relatively large positive value, and this is the signal utilized on line 72 to gate the initialization circuit 52.

The initialization circuit 52 is similar in some respects to the slope sign detection circuit 58, and includes first and second operational amplifiers 140 and 142, an n-channel FET 144 and a p-channel FET 146. The pressure signal is input to the negative input terminal of the first operational amplifier 140 through a resistor 148, and there is a negative feedback path from the output of the amplifier through a resistor 150 and capacitor 152 in parallel to the negative input terminal. The output of the first operational amplifier 140 is also connected through two parallel paths to the negative input terminal of the second operational amplifier 142. One path is through a resistor 154, and the other is through the n-channel FET 144, the drain terminal being connected to the output of the first operational amplifier 140, and the source terminal being connected to the negative input terminal of the second operational amplifier 142. The positive input terminal of the second operational amplifier 142 is grounded, and the output is connected through a resistor 156 to the positive input terminal of the first operational amplifier 140. The second operational amplifier 142 also has a negative feedback path through a capacitor 158. The gate terminal of the n-channel FET 144 is connected to a negative voltage supply through two resistors 160 and 162, the source terminal of the p-channel FET 146 being connected to the junction of the resistors. The drain terminal of the p-channel FET 146 is grounded, and the gate terminal is supplied with a signal from the slope sign detection circuit over line 72 and through a resistor 164.

The second operational amplifier 142 also operates basically as an integrator circuit, and applies to the positive input terminal of the first operational amplifier 140 a signal proportional to the negative of the time integral of the output of the first operational amplifier, multiplied by an integrator gain factor. The gain factor is determined by the reciprocal of the time constant of the integrator circuit, which is the product of the capacitance value of capacitor 158 and the input resistance value. So long as the n-channel FET 144 is in a conductive state, the input resistance value is zero, the gain of the integrator circuit is very large, and the output of the first operational amplifier will be held to zero no matter how the input signal on the negative input terminal of the first operational amplifier 140 varies.

When the slope sign detection circuit 58 detects an inspiratory effort by the patient, and generates a corresponding positive signal on line 72, the p-channel FET 146 will become nonconductive, and the gate terminal of the n-channel FET 144 will therefore be biased negatively, thereby inhibiting conduction through the n-channel FET as well. At this point, the gain of the integrator circuit is determined by the value of the resistor 154 now placed in the circuit. Since this value is relatively large, the integrator gain is relatively low, and the effect of the feedback path through the integrator circuit is relatively insignificant compared with the input signal on the negative input terminal of the first operational amplifier 140. However, the capacitor 158 will retain substantially all of its charge after the n-channel FET 144 is opened, and will have the effect of biasing the positive input terminal of the first operational amplifier 140 just enough to initialize the output signal on line 82 to a zero reference value. Consequently, subsequent variations of the pressure signal input to the negative terminal of the first operational amplifier 140 will be measured at the output terminal with respect to a zero reference point at the time that the n-channel FET 144 was opened. Stated another way, the output signal from the first operational amplifier 140, which is the output signal transmitted through the amplifier 102 to one terminal of the comparator 54, is a signal representative of a difference in absolute pressure as measured from the time of the detected patient inspiratory effort. When this difference reaches a predetermined value, as measured by the comparator 54, the assist signal is generated to initiate an assisted inspiration phase.

It will be appreciated from the foregoing that the present invention represents a substantial advance in the respirator art. In particular, it provides a system for initiating an assisted inspiration phase solely on the basis of a detected demand of the patient in the form of an inspiratory effort, and independently of the absolute pressure at the time of the inspiratory effort. It will also be appreciated that, although a specific embodiment of the invention has been described in detail for purposes of illustration, various modifications and design changes may be made without departing from the spirit and scope of the invention. Accordingly, the invention is not to be limited except as by the appended claims.

I claim:

1. For use in a respiration system, apparatus for detecting a patient's inspiratory effort independently of absolute pressure, said apparatus comprising:
   pressure sensing means, for sensing system pressure near the point of delivery of gas to the patient, including means for generating a pressure signal therefrom;
   first electrical means for generating from said pressure signal a first output signal indicative of a first time differential signal;
   second electrical means for generating a second output signal indicative of the sign of the second time differential of said pressure signal, whereby said second output signal is indicative of an increase in the rate of pressure drop during an expiration phase of the patient breathing cycle;
   third electrical means responsive to said second output signal, for generating a third output signal indicative of the change in the system pressure; and
   comparator means for comparing said third output signal with a reference value indicative of a predetermined pressure drop, and developing a control signal to initiate an assisted inspiration phase of the breathing cycle when said third output signal reaches said reference value.

2. Apparatus as set forth in claim 1, wherein said second electrical means includes timing means for actuating said second electrical means only at a time during the expiration phase when an inspiratory effort is expected.

3. Apparatus as set forth in claim 1, and further including means for varying said reference value of pressure drop and thereby varying the sensitivity of said apparatus.

4. For use in a respiration system, a method for detecting a patient's inspiratory effort independently of absolute pressure, comprising the steps of:
   monitoring system pressure during an expiration phase of the patient breathing cycle and generating a pressure signal indicative of the system pressure;
   differentiating the pressure signal with respect to time, to obtain a first differential pressure signal;
   detecting a change in sign of the slope of the first differential pressure signal;
   detecting a predetermined drop in absolute pressure following the detection of a change in sign of the slope of the first differential pressure signal; and, in response to the detection of the predetermined drop in absolute pressure,
   generating a control signal to be used to initiate an assisted inspiration phase of the breathing cycle, whereby an inspiratory effort by the patient causes an increase in the rate of pressure drop during the expiration phase, the increase being detectable as a change in sign of the slope of the first differential pressure signal, and whereby the detection of the subsequent predetermined pressure drop prevents the initiation of an assisted inspiration phase by spurious fluctuations of the pressure signal.

5. A method as set forth in claim 4, and further including the step of adjusting the sensitivity of said method by varying the predetermined pressure drop.

6. A method as set forth in claim 4, and further including the step of supressing said step of detecting a change in sign of the slope of the first differential pressure signal until an appropriate time in the expiration phase when an inspiratory effort is expected.

7. For use in a respiration system, apparatus for detecting a patient's inspiratory effort independently of absolute pressure, said apparatus comprising:
   means for monitoring pressure in the system and generating an electrical pressure signal therefrom;
   means for differentiating said pressure signal;
   means for detecting a change in sign of the slope of the differentiated pressure signal, and thereby detecting an increased rate of pressure drop due to an inspiratory effort by the patient, said means for detecting a change in sign also generating a first control signal indicative thereof;
   means coupled with said means for detecting a change in sign and responsive to said first control signal, for detecting a predetermined drop in absolute pressure after detection of the change in sign of the slope of the differentiated signal and also generating a second control signal indicative thereof; and means for comparing said second control signal with a reference value indicative of a predetermined pressure drop, whereby the inspiratory effort is unambiguously indicated by a change in sign of the slope of the differentiated pressure signal coupled with a subsequent drop in pressure by the predetermined amount.

8. Apparatus as set forth in claim 7, and further including means for adjusting the sensitivity of said apparatus by varying the predetermined drop in absolute pressure detected by said means for detecting the predetermined drop in absolute pressure.

* * * * *